(12) United States Patent
Thompson et al.

(10) Patent No.: US 8,841,468 B2
(45) Date of Patent: Sep. 23, 2014

(54) SYNTHESIS OF AN AZIDO ENERGETIC ALCOHOL

(75) Inventors: Alicia Thompson, Danvers, MA (US); Ana Racoveanu, Melrose, MA (US); David Skyler, Methuen, MA (US)

(73) Assignee: Physical Sciences, Inc., Andover, MA (US)

( * ) Notice: Subject to any disclaimer, the term of this patent is extended or adjusted under 35 U.S.C. 154(b) by 36 days.

(21) Appl. No.: 12/821,392

(22) Filed: Jun. 23, 2010

(65) Prior Publication Data

US 2011/0319643 A1 Dec. 29, 2011

(51) Int. Cl.
C07C 247/04 (2006.01)

(52) U.S. Cl.
CPC .................. *C07C 247/04* (2013.01)
USPC .......................................... 552/11

(58) Field of Classification Search
USPC .......................................... 552/11
See application file for complete search history.

(56) References Cited

U.S. PATENT DOCUMENTS

| | | | |
|---|---|---|---|
| 2,997,504 A | | 4/1951 | Shechter et al. |
| 3,492,311 A | | 1/1970 | Hamel |
| 3,883,377 A | | 5/1975 | Wright |
| 4,455,508 A | * | 6/1984 | Wesselink ........................ 315/62 |
| 4,472,311 A | | 9/1984 | Frankel et al. |
| 4,795,593 A | * | 1/1989 | Frankel et al. .................. 552/11 |
| 4,797,168 A | * | 1/1989 | Flanagan ........................ 149/88 |
| 4,900,851 A | * | 2/1990 | Frankel et al. .................. 552/12 |
| 4,910,322 A | | 3/1990 | Grakauskas et al. |
| 5,276,171 A | | 1/1994 | Koppes et al. |
| 5,321,143 A | * | 6/1994 | Sharpless et al. ............... 549/34 |
| 5,391,772 A | * | 2/1995 | Thompson et al. ........... 549/492 |
| 6,620,268 B2 | | 9/2003 | Cho et al. |

FOREIGN PATENT DOCUMENTS

WO 2009/072955 6/2009

OTHER PUBLICATIONS

Baum, K., et al., "Novel Approaches to the Synthesis of Fluorodinitromethane and Fluorodinitroethanol" N00014-90-C-0253 (Aug. 1993).
Byun, H-S., et al., "Cyclic Sulfites and Cyclic Sulfates in Organic Synthesis," Tetrahedron 56, pp. 7051-7091 (Apr. 2000).
Davenas, A., "Development of Modern Solid Propellants," J Propulsion and Power, 2003, 19(6), pp. 1108-1128.
Ek, S., et al., "Synthesis and Characterisation of 2,2-dinitro-1,3-propanediol-based Plasticizers," New Trends in Research of Energetic Materials, Proceedings of the Seminar, 8th, Pardubice, Czech Republic, Apr. 19-21, 2005, 1 pp. 180-189.
Weber, J.F., et al., "Synthesis of Novel Energetic Compounds." Propellants, Explosives, Pyrotechnics, vol. 15, No. 1, pp. 26-29 (1990).
Vidari, G., et al., "Desymmetrization of bicyclo[3.3.0]octane-3,7-dione by the Schmidt reaction: an easy synthesis of tecomanine," Tetrahedron: Asymmetry, vol. 8, No. 17, Sep. 11, 1997, pp. 2893-2903.

* cited by examiner

*Primary Examiner* — Sabiha N Qazi
(74) *Attorney, Agent, or Firm* — Proskauer Rose LLP

(57) ABSTRACT

A method of forming an azido energetic alcohol includes converting an energetic diol to a cyclic sulfite, oxidizing the cyclic sulfite to a cyclic sulfate, and opening the cyclic sulfate. The cyclic sulfate is opened, followed by hydrolysis, to form an azido energetic alcohol.

22 Claims, 10 Drawing Sheets

SYNTHESIS OF AN AZIDO ENERGETIC ALCOHOL

STATEMENT OF GOVERNMENT INTEREST

The subject matter described herein was developed in connection with funding provided by the U.S. Army Aviation & Missile Command under Contract No. W31P4Q-09-C-0039. The Federal government may have rights in the technology.

FIELD OF THE INVENTION

This invention relates generally to the synthesis of an azido energetic alcohol, and more particularly, to the synthesis of 3-azido-2,2-dinitropropanol from 2,2-dinitropropane-1,3-diol.

BACKGROUND OF THE INVENTION

Generally, the field of energetic materials uses compounds composed of carbon, hydrogen, nitrogen, and oxygen. These are typically arranged to form explosophoric functionality such as N-nitro, C-nitro, O-nitro, and azido.

Energetic materials containing the geminal dinitro groups ($-C(NO_2)_2$, gem-dinitro) have generally low sensitivity to unplanned stimuli, making them particularly valuable in the creation of munitions meeting Insensitive Munition ("IM") requirements. Additionally, these explosophores are attractive due to their high oxygen content and high energy.

A number of gem-dinitro containing compounds have found application in the production of energetic materials. Typically, these gem-dinitro containing materials are prepared by conversion from a mononitroderivative with an active hydrogen using the silver nitrate method or the potassium ferricyanide method. Alternatively, they may be prepared by functional group manipulation of an existing gem-dinitro containing compound.

Geminal dinitro alcohols such as 2,2-dinitropropanol, 2,2,-dinitrobutanol, and fluorodinitroethanol have the versatility to allow the preparation of a range of energetic plasticizers, binders and oxidizers. For example, 2,2-dinitropropanol is useful in the production of the energetic plasticizers bis(2,2-dinitropropyl formal) ("BDNPF") and bis(2,2-dinitropropylacetal) ("BDNPA").

Although azide groups do not contribute to the oxygen balance of the compounds in which the azide group is contained, organic azides can make an exceptional contribution to the heat of formation (75-95 kcal/mol) and the total energy released upon decomposition. Compounds containing both an azide and gem-dinitro group can possess higher energy than the corresponding azido ($N_3^-$) compounds and thermal stability.

Displacement of leaving groups adjacent to gem-dinitro moieties is known to be difficult due to inductive effects. Previous attempts to create 3-azido 2,2-dinitropropyl chloride by displacement of 1,3 dichloro 2,2-dinitropropane have been unsuccessful for at least this reason. The general approach of preparing 1,2 and 1,3 azido alcohols by displacement of an intermediate cyclic sulfate is well known in organic chemistry.

SUMMARY OF THE INVENTION

A versatile 1-azido 2,2-dinitro containing synthon can be used to create energetic ingredients containing the functionality described above. A gamma azido energetic alcohol can be formed by displacement of an intermediate cyclic sulfate. A gamma azido energetic alcohol is a versatile intermediate that allows for the potential preparation of a wide range of energetic ingredients, including, for example, plasticizers, binders, and oxidizers. Inexpensive starting materials, for example, nitromethane and sodium azide, can be used to synthesize a gamma azido energetic alcohol.

In one aspect, the invention features a method of forming an azido energetic alcohol. The method includes converting an energetic diol to a cyclic sulfite, oxidizing the cyclic sulfite to a cyclic sulfate, and opening the cyclic sulfate to form a non-cyclic sulfate. The non-cyclic sulfate is hydrolyzed subsequent to opening to form an azido energetic alcohol.

In another aspect, the invention features a method of forming an azido energetic alcohol. The method includes reacting thionyl chloride with an energetic diol to form a cyclic sulfite, oxidizing the cyclic sulfite by a ruthenium catalyzed method to form a cyclic sulfate, and reacting the cyclic sulfate with sodium azide followed by hydrolysis to form an azido energetic alcohol.

In some embodiments, the energetic diol is 2,2-dinitropropane-1,3-diol. The cyclic sulfite can be 2,2-dinitro 1,3-propanediol sulfite. In some embodiments, the cyclic sulfate is 2,2-dinitro 1,3-propanediol sulfate. The azido energetic alcohol can be a gamma azido energetic alcohol. The gamma azido energetic alcohol can be 3-azido-2,2-dinitropropanol.

In certain embodiments, the hydrolyzer is sulfuric acid. The cyclic sulfate can be opened by reacting the cyclic sulfate with sodium azide.

In another aspect, the invention features a compound represented by Formula I:

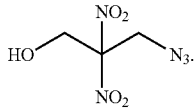

Formula I

In some embodiments, the compound has peaks located at about 4.35, 4,6 and 6.48 ppm in a $^1$H-nuclear magnetic resonance ("NMR") spectrum and peaks located at about 51, 62, and 119 ppm is a $^{13}$C-NMR spectrum.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DESCRIPTION OF THE INVENTION

Figure 1:
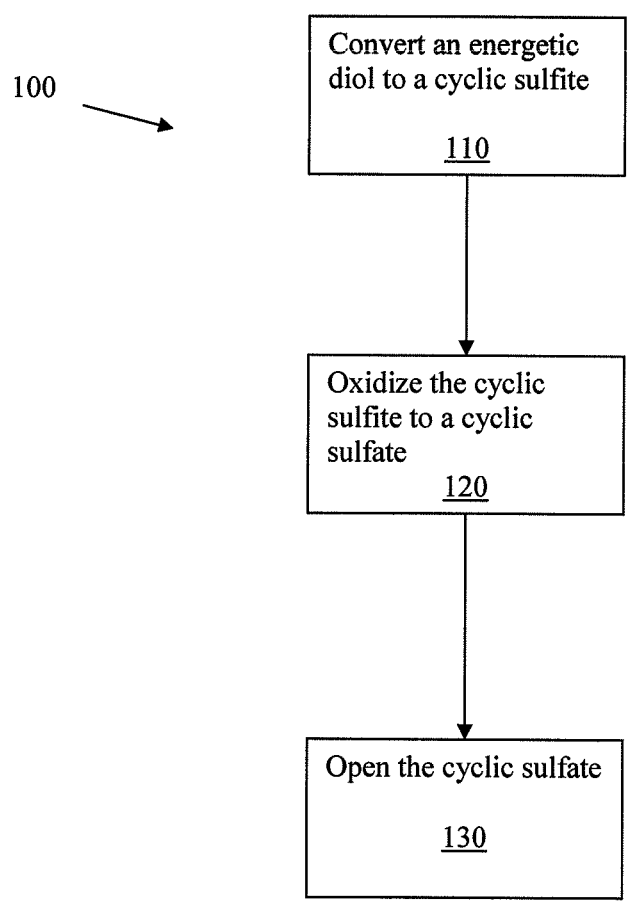
FIG. 1 is a flow chart depicting a method of forming an azido energetic alcohol.

FIG. 1 shows a flow chart of a method 100 of forming an azido energetic alcohol according to an illustrative embodiment of the invention. The azido energetic alcohol can be a gamma azido energetic alcohol. The gamma azido energetic alcohol can be 3-azido-2,2-dinitropropanol as shown in Formula 1.

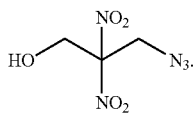

Formula 1

Formula 1, a yellow oil that is soluble in organic solvents, has peaks located at about 4.35, 4.6, and 6.48 ppm in a $^1$H-NMR spectrum and peaks located at about 51, 62, and 119 ppm in a $^{13}$C-NMR spectrum as discussed with reference to FIGS. 2B and 3B below. Formula 1 can be formed through a cyclic sulfate intermediate as shown in Scheme 1. Numerous ingredients and intermediates for the preparation of energetic compositions can be prepared using the compound of Formula 1. Functionalization of the terminal hydroxyl group of Formula 1 can provide functional handles for further elaboration, for example, sulfonation, arylation, alkylation, nitration, displacement or other transformation is possible. In addition, the cluster of energetic groups in a relatively small area, while maintaining the stability of the molecule, further enhances the benefits of 3-azido-2,2-dinitropropanol.

In some embodiments, substitution on the methylene carbons is possible. Formula 2 represents substitution on the methylene carbons. In Formula 2, either m or n can be at least one. In some embodiments, both m and n are at least 1 and in some embodiments, only one of m or n is at least 1.

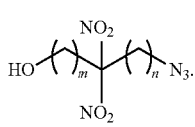

Formula 2

In Formula 3, R can be a functionalized or unfunctionalized alkyl, aryl, or herteroaryl group. In some embodiments, one R group is a hydrogen atom while the other R group is a functionalized or unfunctionalized alkyl, aryl, or herteroaryl group. The R groups can be the same, or the R groups can be different. For example, one R group could be an alkyl group while the other R group is an aryl group.

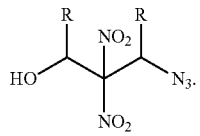

Formula 3

Forming 3-azido-2,2-dinitropropanol, Formula 1, through a cyclic sulfate intermediate is advantageous because the reactions are relatively quick and require only mild conditions. For example, 40° C. is the highest temperature that is used. In addition, the reactions do not require anhydrous conditions. The yields for the first two steps of Scheme 1 are high. For example, the yield can be greater than 80%. The overall yield of the product, 3-azido-2,2-dinitropropanol, can be greater than 60% when 2,2-dinitropropanediol is used as the starting material.

SCHEME 1

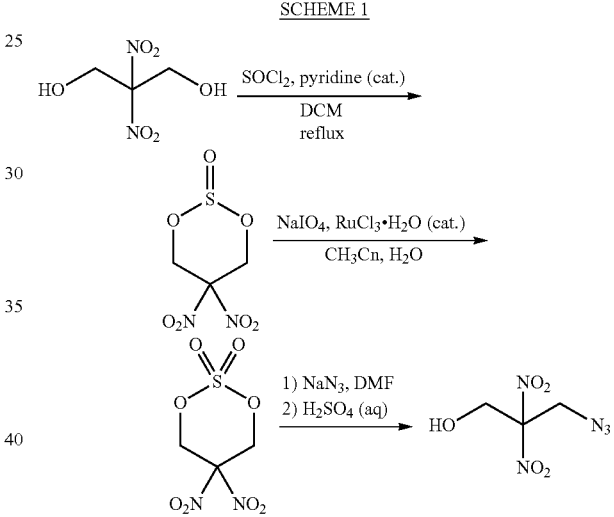

Referring to FIG. 1 and Scheme 1, an azido energetic alcohol can be formed by converting an energetic diol to a cyclic sulfite (step 110). As shown in Scheme 1, the energetic diol is 2,2-dinitropropane-1,3-diol, and the cyclic sulfite is 2,2-dinitro 1,3-propanediol sulfite. The energetic diol is reacted with thionyl chloride to form the cyclic sulfite.

Next, the cyclic sulfite can be oxidized to form a cyclic sulfate (step 120). As shown in Scheme 1, the cyclic sulfate is 2,2-dinitro 1,3-propanedio sulfate. The cyclic sulfite is oxidized by a ruthenium catalyzed method to form a cyclic sulfate.

The cyclic sulfate can be opened (step 130), followed by hydrolysis, to form an azido energetic alcohol. As shown in Scheme 1, the azido energetic alcohol is a gamma azido energetic alcohol. Also, as shown in Scheme 1, the hydrolyzer is sulfuric acid. The hydrolyzer can be 20% sulfuric acid.

The cyclic sulfate can be opened by reacting the cyclic sulfate with sodium azide. The sulfate can be readily converted into a gamma azido energetic alcohol, for example, 3-azido 2,2-dinitropropanol, by displacement with sodium azide followed by solvolysis.

Scheme 2 illustrates the conversion of nitromethane into 2,2-dinitro 1,3-propanediol cyclic sulfate. Nitromethane, an inexpensive starting material, can be converted to 2,2,-dinitropropane-1,3-diol by first reacting the nitromethane with formaldehyde and sodium hydroxide and then adding sodium nitrite and silver nitrate. The conversion of 2,2-dinitropropane-1,3-diol to 2,2-dinitro 1,3-propanediol cyclic sulfate proceeds as illustrated in Scheme 2.

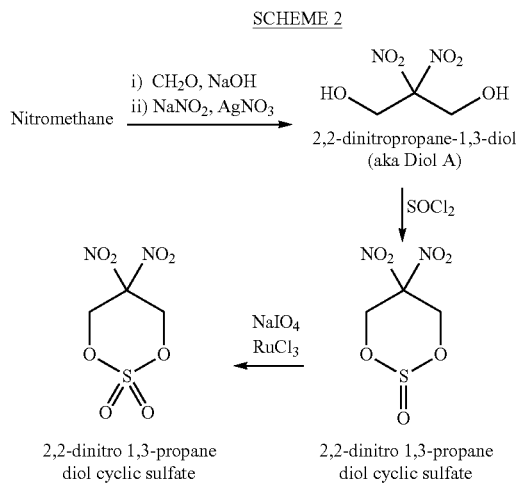

Scheme 3 illustrates the conversion of 2,2-dinitro 1,3-propanediol cyclic sulfate into 3-azido 2,2-dinitropropanol. First, 2,2-dinitro 1,3-propanediol cyclic sulfate is reacted with sodium azide and dimethylformamide ("DMF") to open the cyclic sulfate and form sodium 3-azido-2,2-dinitropropyl sulfate. After the cyclic sulfate is opened, the sodium 3-azido-2,2-dinitropropyl sulfate is reacted with 20% sulfuric acid to form 3-azido-2,2-dinitropropanol.

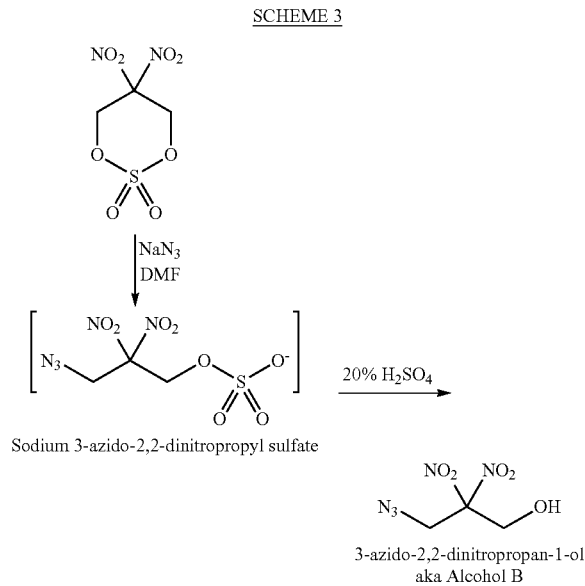

Figure 2B:
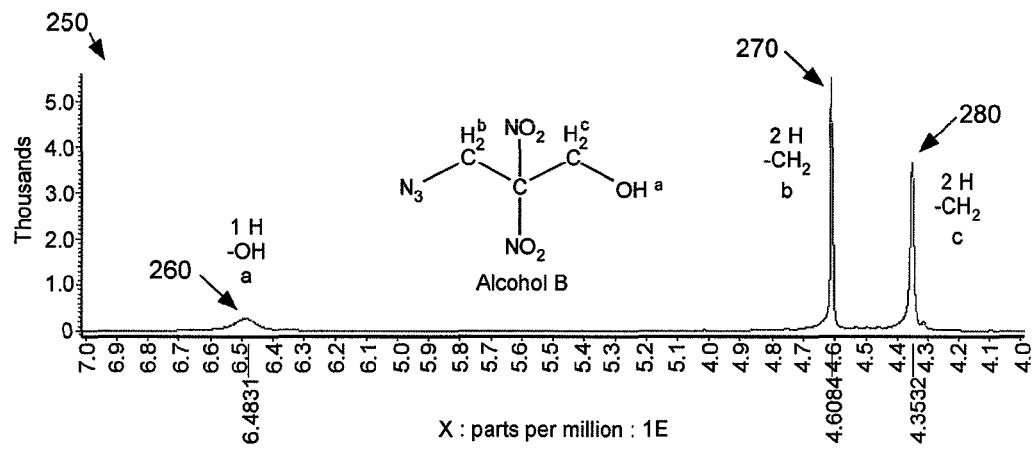
FIG. 2B is a $^1$H-NMR spectrum of 3-azido-2,2-dinitropropanol.
Figure 2A:
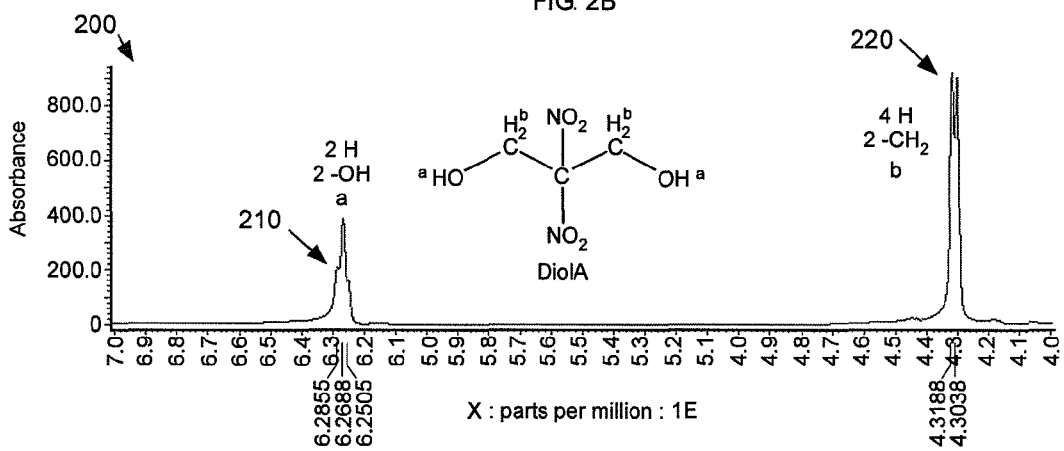
FIG. 2A is a $^1$H-NMR spectrum of 2,2-dinitropropane-1,3-diol.

FIG. 2A is a $^1$H-NMR spectrum 200 of 2,2-dinitropropane-1,3-diol. FIG. 2B is a $^1$H-NMR spectrum 250 of 3-azido-2,2-dinitropropanol. A comparison of FIG. 2A and FIG. 2B demonstrates the destruction of the symmetry observed for Diol A (2,2-dinitropropane-1,3-diol) by the insertion of the azide group in Alcohol B (3-azido-2,2-dinitropropanol). Referring to FIG. 2A, the symmetry of hydrogen atoms of Diol A is shown. The two hydrogen atoms of the two OH groups are represented by a single absorbance 210 at about 6.26 ppm. Since these two hydrogen atoms give rise to a single absorbance, the two hydrogen atoms are chemically equivalent. In addition, the four hydrogen atoms of the two methylene groups are represented by an absorbance 220 at about 4.3 ppm. Since these four hydrogen atoms give rise to a single absorbance, the four hydrogen atoms are chemically equivalent. Furthermore, absorbance 220 is more intense than absorbance 210, indicating that absorbance 220 accounts for more hydrogen atoms than absorbance 210. Absorbance 220 accounts for four hydrogen atoms while absorbance 210 accounts for only two hydrogen atoms.

The $^1$H-NMR spectrum 250 of FIG. 2B shows the destruction of the symmetry that is present in the $^1$H-NMR spectrum 200 of FIG. 2A. The single hydrogen atom of the OH group is represented by a single absorbance 260 at about 6.48 ppm. The intensity of the absorbance 260 is much less than the intensity of the absorbance 210 of FIG. 2A because the intensity of the absorbance 260 represents one hydrogen atom while the intensity of the absorbance 210 represents two hydrogen atoms.

The lack of symmetry of Alcohol B is better shown by comparing the hydrogen atoms of the two methyl groups. While all four hydrogen atoms of the two methyl groups of Diol A resulted in a single peak, the four hydrogen atoms of Alcohol B result in two peaks. A first peak at an absorbance 270 of about 4.6 represents the hydrogen atoms of the methyl group closest to the azide group, while a second peak at an absorbance 280 of about 4.35 represents the hydrogen atoms of the methyl group closest to the OH group. These two separate peaks 270, 280 represent the destruction of symmetry that is present in FIG. 2A and also represent the formation of the desired end product, 3-azido-2,2-dinitropropanol.

Figure 3B:
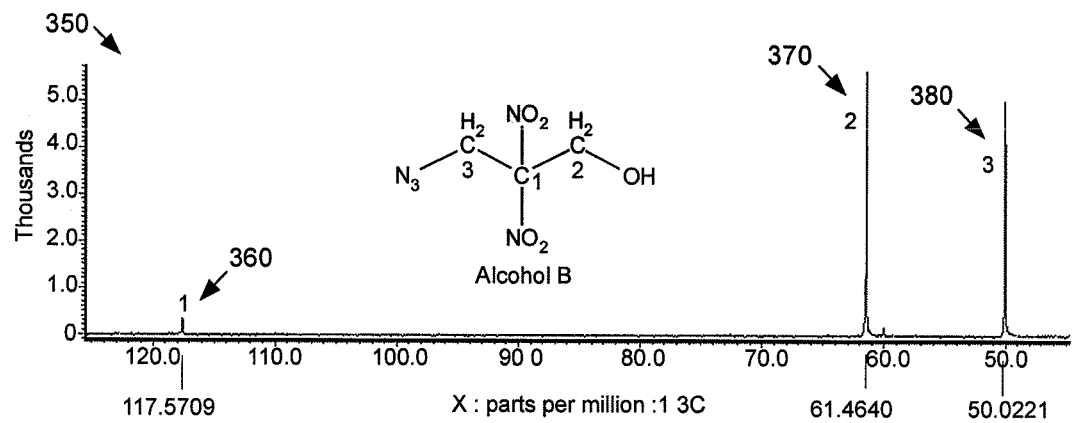
FIG. 3B is a $^{13}$C-NMR spectrum of 3-azido-2,2-dinitropropanol.
Figure 3A:
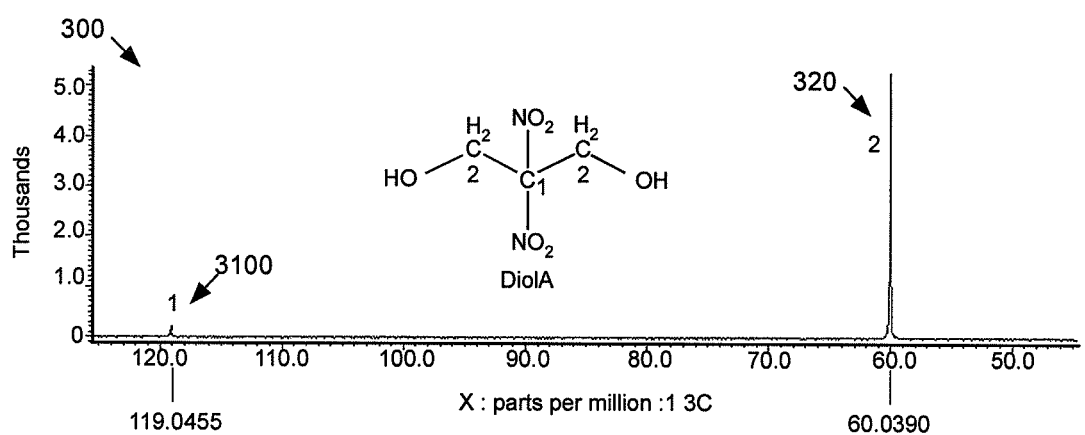
FIG. 3A is a $^{13}$C-NMR spectrum of 2,2-dinitropropane-1,3-diol.

The loss of symmetry can be further demonstrated by comparing FIG. 3A, a $^{13}$C-NMR spectrum 300 of 2,2-dinitropropane-1,3-diol, with FIG. 3B, a $^{13}$C-NMR spectrum 350 of 3-azido-2,2-dinitropropanol. Referring to FIG. 3A, the symmetry of the carbon atoms is shown. The center carbon atom is represented by a low intensity absorbance 310 at about 119 ppm. The other two carbon atoms in Diol A are chemically equivalent and are represented by a single absorbance 320 at about 60.0 ppm. FIG. 3B shows three separate absorbance peaks 360, 370, 380, which represent the three chemically distinct carbon atoms of 3-azido-2,2-dinitropropanol. Similar to absorbance 310 of FIG. 3A, absorbance 360 at about 117.5 ppm represents the center carbon atom of Alcohol B. However, the other two carbon atoms are shown as distinct absorbance peaks 370, 380, because the two carbon atoms are not chemically equivalent. The carbon atom that is closest to the OH group is depicted by an absorbance peak 370 at about 61.5 ppm. The carbon atom that is closest to the azide group is depicted by an absorbance peak 380 at about 50.0 ppm. These two separate absorbance peaks 370, 380, instead of a single peak, for example, absorbance peak 320 of FIG. 3A, represent the destruction of symmetry and the formation of the desired end product, 3-azido-2,2-dinitropropanol.

Figure 4:
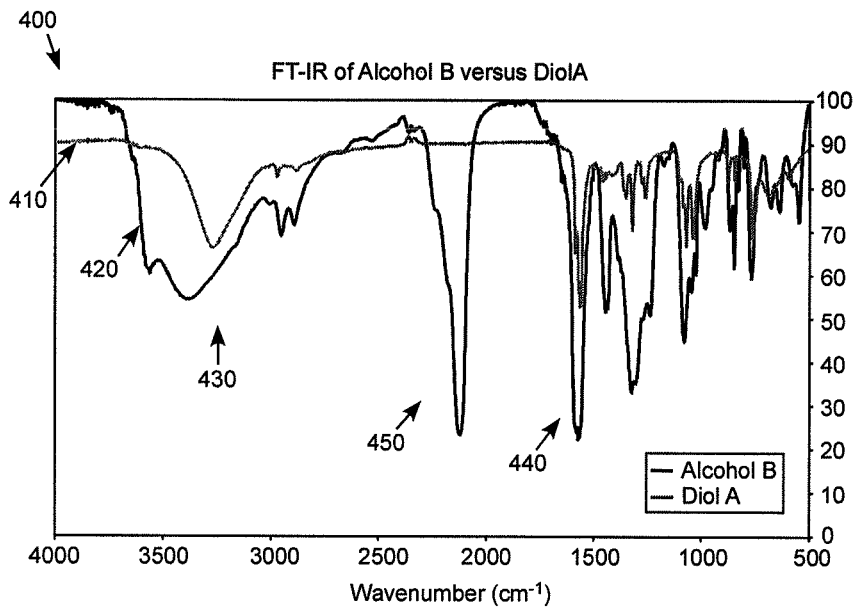
FIG. 4 is an FT-IR spectrum of 2,2-dinitropropane-1,3-diol and 3-azido-2,2-dinitropropanol.

FIG. 4 is a Fourier transform spectroscopy ("FT-IR") spectrum 400 of 2,2-dinitropropane-1,3-diol, or Diol A depicted by curve 410, and 3-azido-2,2-dinitropropanol, or Alcohol B depicted by curve 420. The product, Alcohol B, has many peaks in common with the starting material, Diol A, specifically the alcohol stretch 430 at about 3300 cm$^{-1}$ and the aliphatic nitro peak 440 at about 1580 cm$^{-1}$. The spectrum of the product, Alcohol B, contains one major peak 450 at about 2100 cm$^{-1}$ that is not present in the Diol A spectrum. The peak 450 corresponds to the azide group that is present in 3-azido-2,2-dinitropropanol, which is not present in 2,2-dinitropropane-1,3-diol.

EXAMPLE 1

2,2 dinitropropane-1,3-diol (35.8 g, 215 mmol) was suspended in dichloromethane ("DCM") (Anhydrous, 200 mL) in a 1 L 2 neck round bottom flask fitted with a condenser, internal thermometer and magnetic stirring. The solution was warmed to reflux under argon, and $SOCl_2$ (1.3 eq., 279.5 mmol. 20.34 mL) was added dropwise to the refluxing solution over 10 minutes. The faint yellow solution with trace solids was held at reflux for an additional 10 minutes, and pyridine (2 mol %, 4.3 mmol, 340 mg) in 7 mL dry $CH_2Cl_2$ was added dropwise. After 2.5 hours at reflux, the faintly yellow clear solution was cooled on ice, and deionized $H_2O$ (300 mL) was added slowly with stirring. The organic layer was separated, and washed with sat. $NaHCO_3$ (200 mL) followed by deionized $H_2O$ (200 mL). After drying with sodium sulfate, the solvent was removed under reduced pressure to provide a light tan solid (43 g). The crude product was dissolved in $Et_2O$ (150 mL), and hexane (150 mL) was added. The solution was decanted away from trace orange solids that immediately precipitated. An additional portion of hexane (80 mL) was added, and the solution was slowly cooled to yield a total of 40.3 g (82% yield) of off-white crystals, M.P. 37-39° C.

Figure 5:
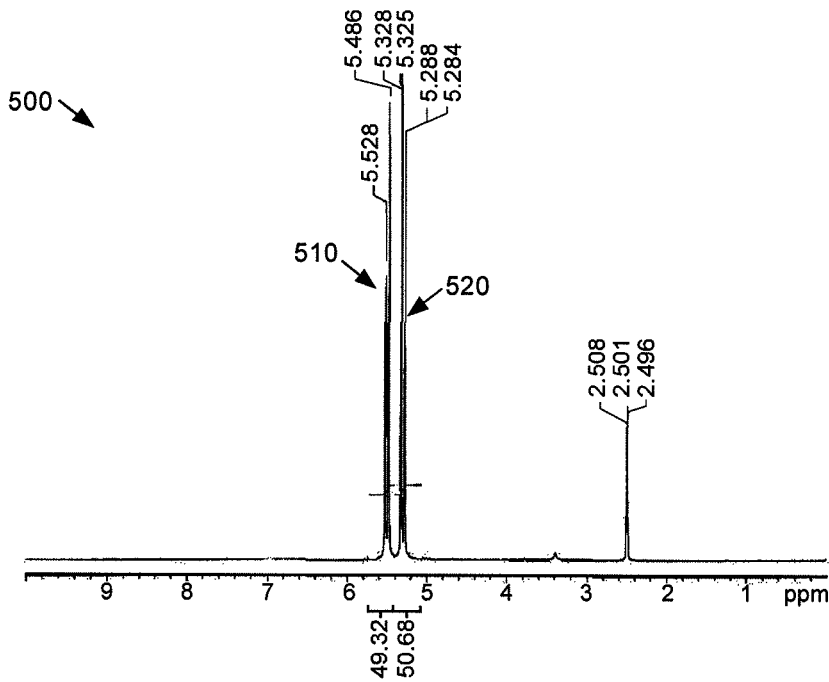
FIG. 5 is a $^1$H-NMR spectrum of a cyclic sulfite.

$^1$H-NMR, $^{13}$C-NMR, and FT-IR spectra were obtained from the white crystals, which show that a cyclic sulfite was formed. FIG. 5 is a $^1$H NMR spectrum 500 of a cyclic sulfite. The $^1$H NMR spectrum 500 shows two distinct absorbance peaks, one absorbance peak 510 at about 5.51 ppm and one absorbance peak 520 at about 5.21 ppm. These peaks are indicative of the inequivalent protons on the same side as, and opposite to, the sulfite oxygen.

Figure 6:
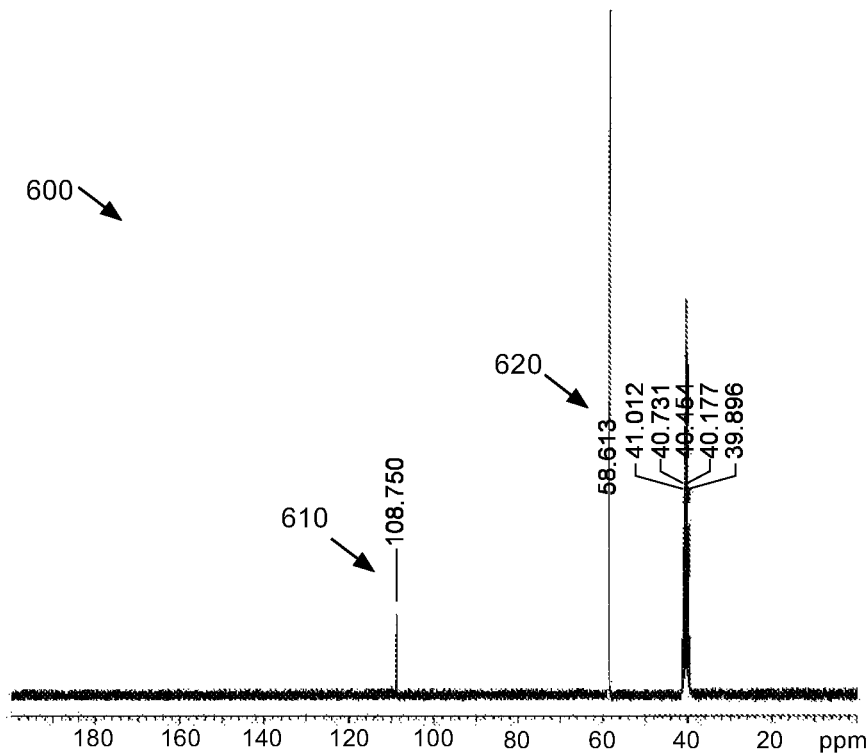
FIG. 6 is a $^{13}$C-NMR spectrum of a cyclic sulfite.

FIG. 6 is a $^{13}$C-NMR spectrum 600 of a cyclic sulfite. The $^{13}$C-NMR spectrum 600 also shows two distinct absorbance peaks, one absorbance peak 610 at about 116 ppm and one absorbance peak 620 at about 58 ppm. These peaks are indicative of the gem-dinitro carbon and the two equivalent methylene carbons, respectively.

Figure 7:
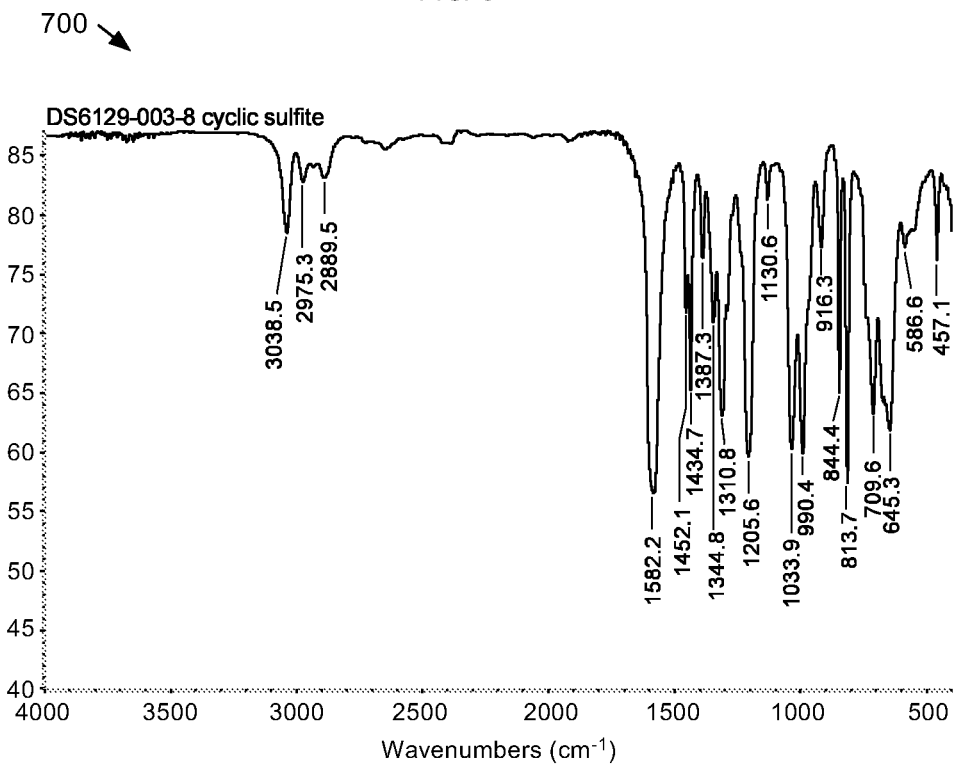
FIG. 7 is an FT-IR spectrum of a cyclic sulfite.

FIG. 7 is an FT-IR spectrum 700 of a cyclic sulfite. This spectrum indicates the absence of hydroxyl group stretch present in the precursor, and the presence of the sulfite by its stretch at approximately 1205 cm$^{-1}$.

EXAMPLE 2

The cyclic sulfite from Example 1 (40 g, 0.189 mol) was dissolved in $CH_3CN$ (220 mL) in a 1 L 3 neck flask with overhead stirring and internal thermometer. $NaIO_4$ (1.5 eq., 283.5 mmol, 60.6 g) was added followed by dI $H_2O$ (308 mL). The suspension was placed in a room temperature water bath, and $RuCl_3 \cdot H_2O$ (0.01 eq. 1.89 mmol, 426 mg) was added. The suspension immediately turned brown and became thick with solids. A small exotherm pushed the reaction temperature up to 42° C., but the temperature rapidly dropped back down to 30° C. After stirring for 2 hours, the solution was extracted with $Et_2O$ (3×700 mL) and washed with dI $H_2O$ (500 mL), followed by sat. $NaHCO_3$ (500 mL), dI $H_2O$ (200 mL), and finally brine (500 mL). The organics were dried with sodium sulfate, and solvent was removed. The crude solids were crystallized from $Et_2O$/hexanes to provide the product as bright white crystals (40 g, 175 mmol, 93%) having a melting temperature between 63-66° C.

Figure 8:
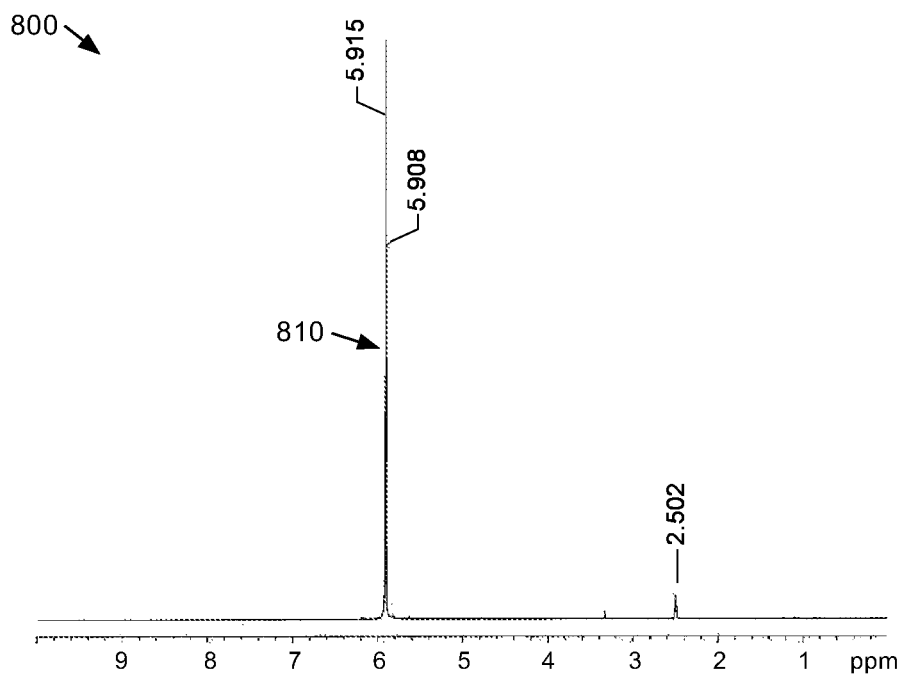
FIG. 8 is a $^1$H-NMR spectrum of a cyclic sulfate.

$^1$H-NMR, $^{13}$C-NMR, and FT-IR spectra were obtained from the bright white crystals which show that a cyclic sulfate was formed. FIG. 8 is a $^1$H-NMR spectrum 800 of a cyclic sulfate. The $^1$H-NMR spectrum 800 shows one distinct absorbance peak 810 at about 5.9 ppm. This peak is indicative of the equivalent methylene protons of the cyclic sulfate.

Figure 9:
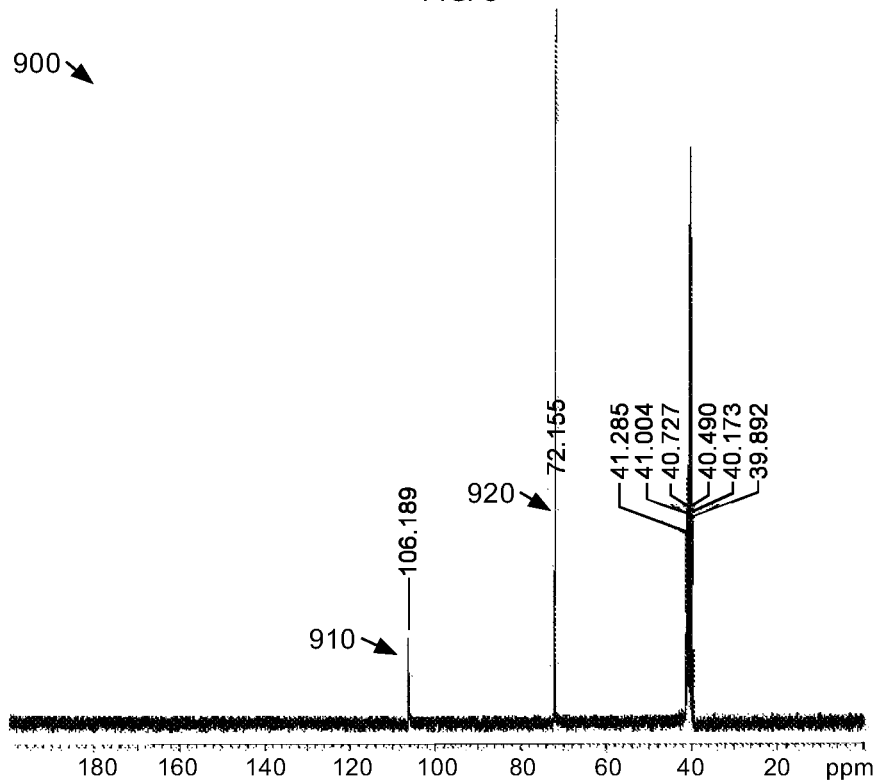
FIG. 9 is a $^{13}$C-NMR spectrum of a cyclic sulfate.

FIG. 9 is a $^{13}$C-NMR spectrum 900 of a cyclic sulfate. The $^{13}$C-NMR spectrum 900 shows two distinct absorbance peaks, one absorbance peak 910 at about 119 ppm and one absorbance peak 920 at about 72 ppm. These peaks are indicative of the gem-dinitro carbon and methylene carbons of the cyclic sulfate.

Figure 10:
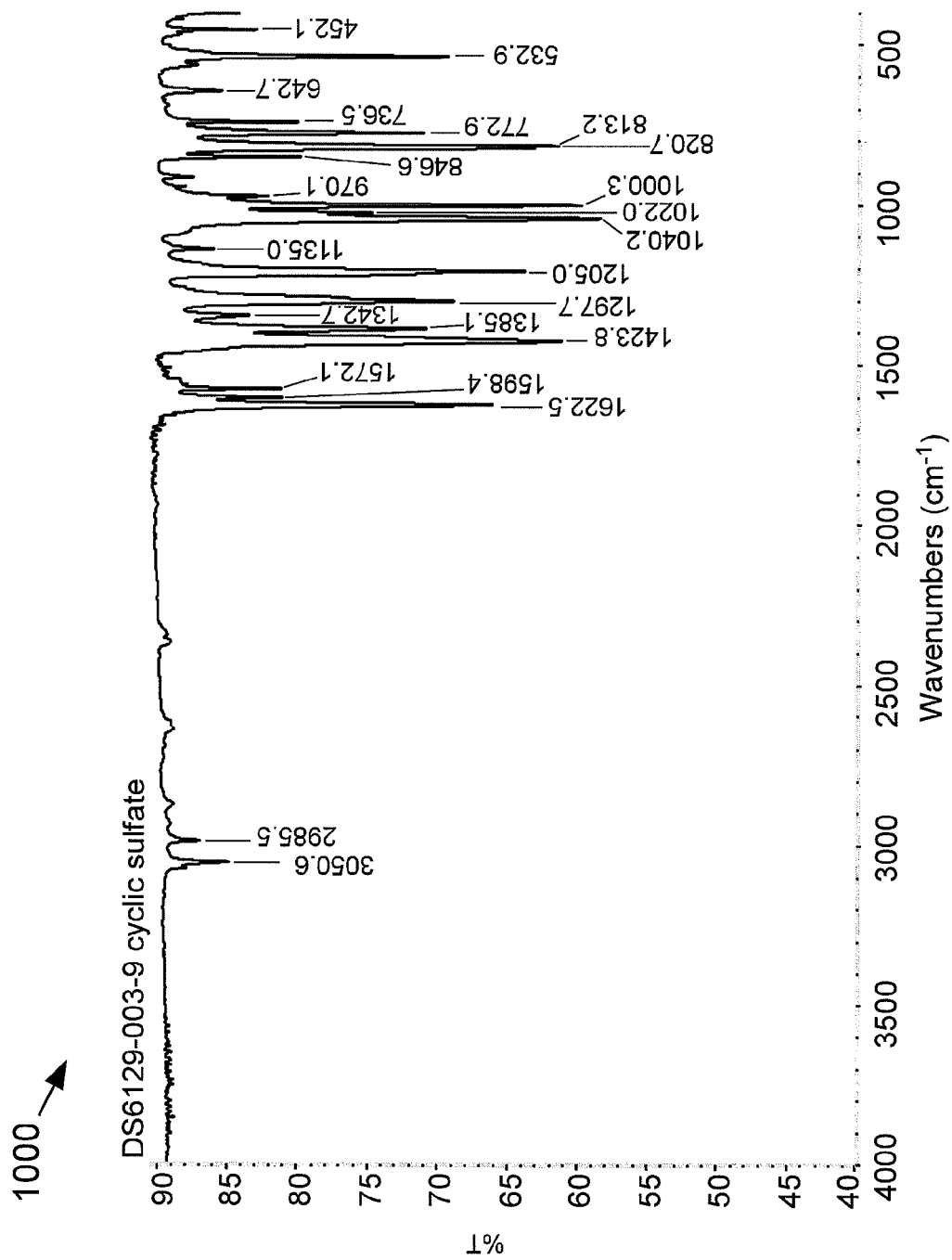
FIG. 10 is an FT-IR spectrum of a cyclic sulfate.

FIG. 10 is an FT-IR spectrum 1000 of a cyclic sulfate. The new stretch at 1423 cm$^{-1}$ is indicative of the presence of the cyclic sulfate functionality.

EXAMPLE 3

The cyclic sulfate produced in Example 2 (20 g, 87.6 mmol) was dissolved in DMF (Anhydrous, 200 mL) in a 500 mL round bottomed flask with internal thermometer and magnetic stirring. The flask was submerged in a room temperature water bath, and $NaN_3$ (1.1 eq. 96.4 mmol 6.26 g) was added.

After 1.75 hours, the majority of the solvent was removed from the clear yellow solution under reduced pressure. The white semisolid that resulted totaled 45 g including residual DMF.

Figure 11:
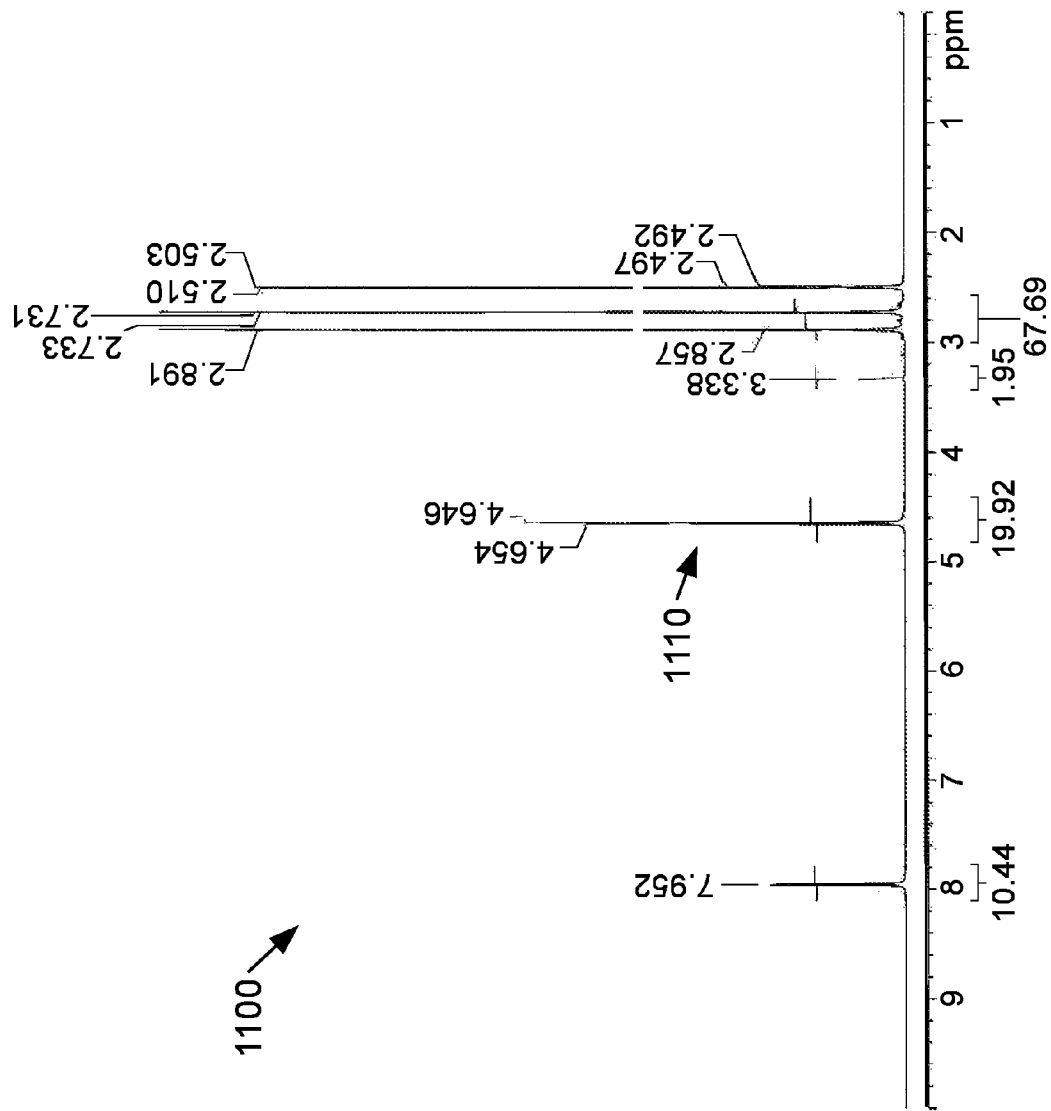
FIG. 11 is a $^1$H-NMR spectrum of a white semisolid including residual DMF.

FIG. 11 is a $^1$H-NMR spectrum 1100 of the white semisolid including residual DMF. There is one significant absorbance peak 1110 at about 4.65 ppm on the $^1$H-NMR spectrum 1100.

The crude material from the previous step was cooled in an ice-bath, and 100 mL of 20% $H_2SO_4$ was added. The solution was stirred in the ice bath for 5 minutes and warmed to room temperature and then 30° C. The product was isolated in crops by extraction with $Et_2O$, and the pooled organics were dried with sodium sulfate. After removal of solvent, the product was isolated in pure form as a yellow oil (14 g, 73.3 mmol) in 84% yield.

Figure 12:
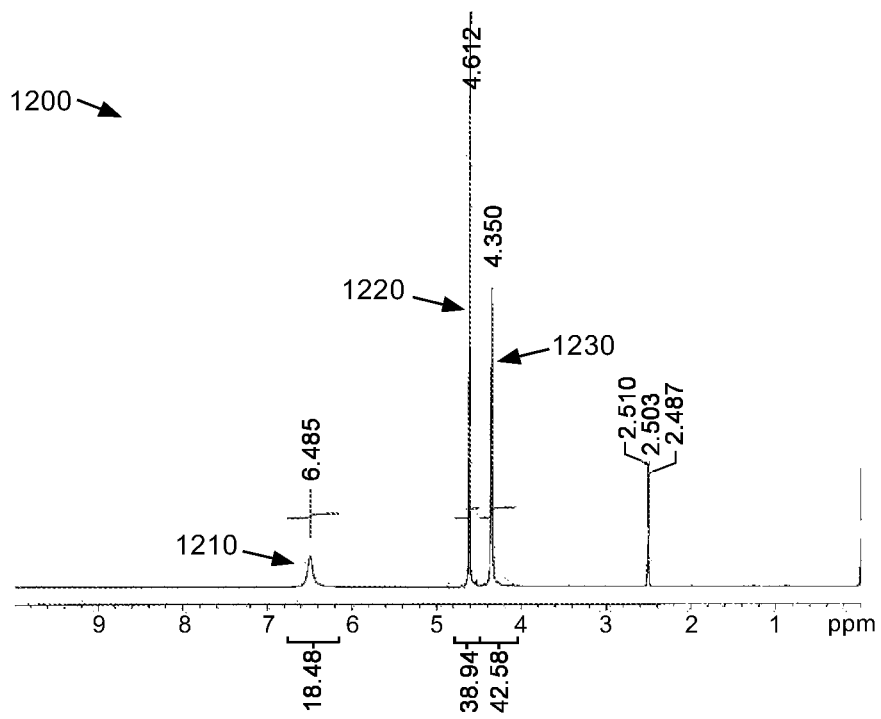
FIG. 12 is a $^1$H-NMR spectrum of the isolated yellow oil, 3-azido-2,2-dinitropropanol.

FIG. 12 is a $^1$H-NMR spectrum 1200 of the isolated yellow oil. Similar to FIG. 2B, $^1$H-NMR spectrum 1200 has three distinct absorbance peaks, one absorbance peak 1210 at about 6.4 ppm, one absorbance peak 1220 at about 4.6 ppm, and one absorbance peak 1230 at about 4.35 ppm. The single hydrogen atom of the OH group is represented by a single absorbance 1210 at about 6.4 ppm. The two other absorbance peaks 1220, 1230 represent four hydrogen atoms. The peak at an absorbance 1220 of about 4.6 ppm represents the hydrogen atoms of the methyl group closest to the azide group, and the absorbance peak 1230 of about 4.35 ppm represents the hydrogen atoms of the methyl group closest to the OH group. These two separate peaks 1220, 1230 represent the formation of the desired end product, 3-azido-2,2-dinitropropanol.

Figure 13:
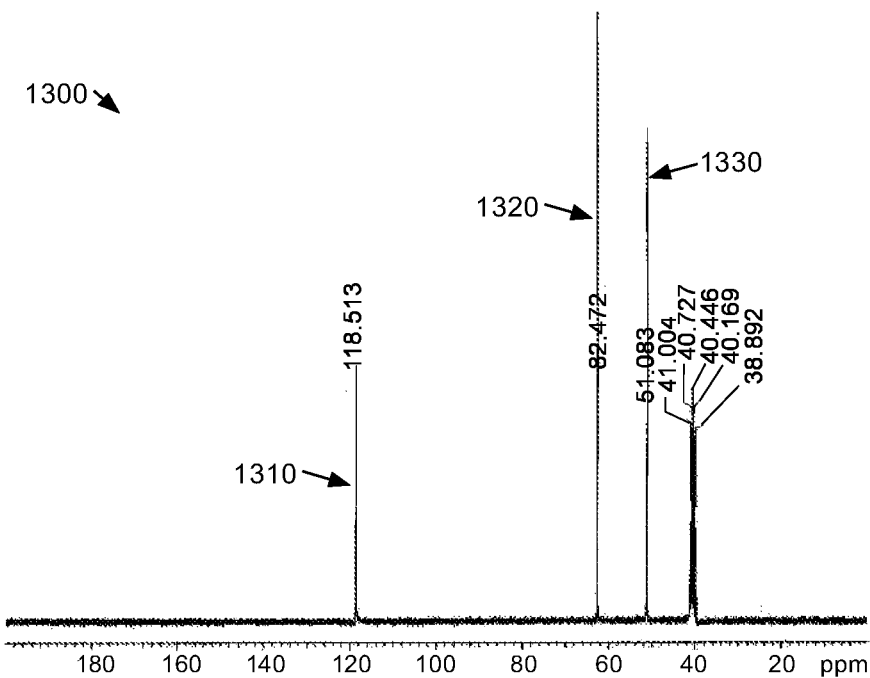
FIG. 13 is a $^{13}$C-NMR spectrum of the isolated yellow oil, 3-azido-2,2-dinitropropanol.

FIG. 13 is a $^{13}$C-NMR spectrum 1300 of the isolated yellow oil. Similar to FIG. 3B, FIG. 13 shows three separate absorbance peaks, 1310, 1320, 1330, which represent the three chemically distinct carbon atoms of the desired product, 3-azido-2,2-dinitropropanol. Absorbance peak 1310 at about 118.5 ppm represents the center carbon atom of the desired product. Absorbance peak 1320 at about 62 ppm represents the carbon atom that is closest to the OH group of the desired end product, 3-azido-2,2-dinitropropanol. Absorbance peak 1330 at about 51 ppm represents the carbon atom that is closest to the azide group of the desired end product, 3-azido-2,2-dinitropropanol.

Figure 14:
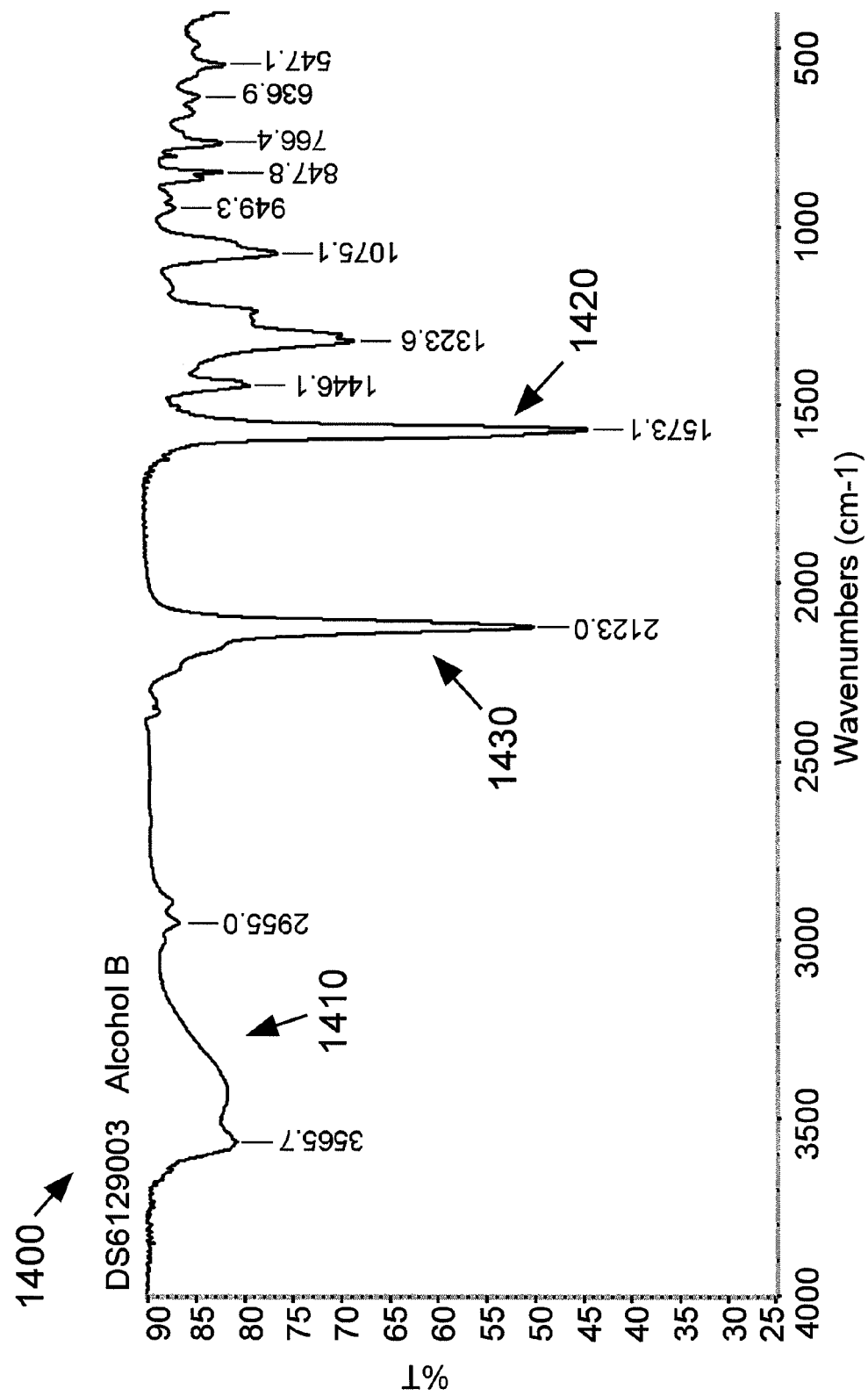
FIG. 14 is an FT-IR spectrum of the isolated yellow oil, 3-azido-2,2-dinitropropanol.

FIG. 14 is an FT-IR spectrum 1400 of the isolated yellow oil. Similar to FIG. 4, FIG. 14 shows an alcohol peak 1410 at about 3300 cm$^{-1}$ and an aliphatic nitro peak 1420 at about 1580 cm$^{-1}$. FT-IR spectrum 1400 also includes a peak 1430 at about 2100 cm$^{-1}$, which represents the presence of an azide group.

Based on the $^1$H-NMR, $^{13}$C-NMR, and FT-IR data collected, it is believed that Alcohol B was formed from Diol A in an efficient manner through a cyclic sulfate intermediate. By crystallization of the intermediate sulfite and sulfate, purification of the final Alcohol B product is unnecessary. Overall yields by this process are in excess of 60% for 2,2-dinitropropanediol.

All numbers expressing quantities of ingredients, constituents, temperature, volumes, other reaction parameters, etc., used in the above three examples, are to be understood as being modified in all instances by the word "about." Any numerical value, however, inherently contains certain errors necessarily resulting from the standard deviation found in the testing measurements.

Although various aspects of the disclosed method have been shown and described, modifications may occur to those skilled in the art upon reading the specification. The present application includes such modifications and is limited only by the scope of the claims.

What is claimed is:

1. A method of forming a gem-dinitro azido energetic alcohol, the method comprising:
   converting a gem-dinitro energetic diol to a gem-dinitro cyclic sulfite;
   oxidizing the gem-dinitro cyclic sulfite to a gem-dinitro cyclic sulfate; and
   opening the gem-dinitro cyclic sulfate to form a gem-dinitro non-cyclic sulfate; and
   hydrolyzing the gem-dinitro non-cyclic sulfate to form the gem-dinitro azido energetic alcohol.

2. The method of claim 1 wherein the energetic diol is 2,2-dinitropropane-1,3-diol.

3. The method of claim 1 wherein the cyclic sulfite is 2,2-dinitro 1,3-propanediol sulfite.

4. The method of claim 1 wherein the cyclic sulfate is 2,2-dinitro 1,3-propanediol sulfate.

5. The method of claim 1 wherein the hydrolyzer is sulfuric acid.

6. The method of claim 1 wherein the cyclic sulfate is opened by reacting the cyclic sulfate with sodium azide.

7. The method of claim 1 wherein the azido energetic alcohol is a gamma azido energetic alcohol.

8. The method of claim 7 wherein the gamma azido energetic alcohol is 3-azido-2,2-dinitropropanol.

9. A method of forming a gem-dinitro azido energetic alcohol containing a geminal dinitro group, the method comprising:
   reacting thionyl chloride with a gem-dinitro energetic diol to form a gem-dinitro cyclic sulfite;
   oxidizing the gem-dinitro cyclic sulfite by a ruthenium catalyzed method to form a gem-dinitro cyclic sulfate; and
   reacting the gem-dinitro cyclic sulfate with sodium azide in the presence of a hydrolyzer to form the gem-dinitro azido energetic alcohol.

10. The method of claim 9 wherein the hydrolyzer is sulfuric acid.

11. The method of claim 9 wherein the azido energetic alcohol is gamma azido energetic alcohol.

12. The method of claim 11 wherein the gamma azido energetic alcohol is 3-azido-2,2-dinitropropanol.

13. A compound represented by Formula I:

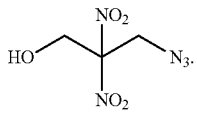

Formula I

14. The compound of claim 13 wherein the compound has a first peak located at about 4.6 ppm on a $^1$H-NMR and a second peak located at about 50 ppm on a $^{13}$C-NMR.

15. The method of claim 1 wherein the energetic diol is a geminal dinitro energetic diol.

16. The method of claim 1 wherein the energetic diol is a geminal dinitro energetic diol.

17. The method of claim 9 wherein the energetic diol is a geminal dinitro energetic diol.

18. The method of claim 9 wherein the energetic diol is a geminal dinitro energetic diol.

19. The method of claim 1 wherein oxidizing the cyclic sulfite to the cyclic sulfate occurs at temperatures between 30° C. to 42° C. for approximately 2 hours.

20. The method of claim 9 wherein oxidizing the cyclic sulfite to the cyclic sulfate occurs at temperatures between 30° C. to 42° C. for approximately 2 hours.

21. The method of claim 1 wherein at least one of the cyclic sulfite or cyclic sulfate is a six-membered ring structure.

22. The method of claim 9 wherein at least one of the cyclic sulfite or cyclic sulfate is a six-membered ring structure.

\* \* \* \* \*